US010427149B2

(12) United States Patent
Efinger et al.

(10) Patent No.: US 10,427,149 B2
(45) Date of Patent: Oct. 1, 2019

(54) LABORATORY CABINET

(71) Applicant: Binder GmbH, Tuttlingen (DE)

(72) Inventors: Patrick Efinger, Balgheim (DE); Ewald Storz, Rietheim-Weilheim (DE); Peter M. Binder, Altnau (CH); Eugen Baumgärtner, Villingen-Schwenningen (DE)

(73) Assignee: Binder GmbH, Tuttlingen (DE)

( * ) Notice: Subject to any disclaimer, the term of this patent is extended or adjusted under 35 U.S.C. 154(b) by 0 days.

(21) Appl. No.: 15/965,443

(22) Filed: Apr. 27, 2018

(65) Prior Publication Data
US 2018/0311659 A1 Nov. 1, 2018

(30) Foreign Application Priority Data

Apr. 28, 2017 (DE) .................. 10 2017 109 262
Feb. 16, 2018 (EP) ........................... 18000153

(51) Int. Cl.
*B01L 1/02* (2006.01)
*B01L 9/00* (2006.01)
(Continued)

(52) U.S. Cl.
CPC ............. *B01L 1/025* (2013.01); *B01L 9/00* (2013.01); *C12M 41/14* (2013.01); *E05C 1/08* (2013.01);
(Continued)

(58) Field of Classification Search
CPC ........... B01L 1/025; C12M 41/14; E05C 1/08; E05C 3/044; E05C 7/02; E05C 19/16
See application file for complete search history.

(56) References Cited

U.S. PATENT DOCUMENTS 4,302,907 A * 12/1981 Canals ................ E05C 7/02
292/150
4,771,269 A * 9/1988 Pasty ................ E05B 17/22
200/61.69
(Continued)

FOREIGN PATENT DOCUMENTS

DE    19803601         9/1999
DE    19803601 C1      9/1999
(Continued)

OTHER PUBLICATIONS

European Patent Office, "Search Report" issued in European patent application No. 18000153.9, dated Aug. 22, 2018, document of 7 pages.
(Continued)

*Primary Examiner* — Daniel J Rohrhoff
(74) *Attorney, Agent, or Firm* — Akerman LLP; Peter A. Chiabotti

(57) ABSTRACT

A laboratory cabinet, for instance a cold chamber, a heating cabinet, a drying cabinet, or an incubator, can have a housing featuring at least one exterior door, featuring at least one interior space which can be closed by means of an interior door, such that the laboratory cabinet features adjustable means, such that as a function of the position of the means, the interior door can be opened together with the exterior door or independently of the exterior door, such that the means are inaccessible when the exterior door is closed.

20 Claims, 4 Drawing Sheets

(51) Int. Cl.
*E05C 1/08* (2006.01)
*C12M 1/00* (2006.01)
*E05C 3/04* (2006.01)
*E05C 7/02* (2006.01)
*E05C 19/16* (2006.01)
*E05B 65/00* (2006.01)

(52) U.S. Cl.
CPC ............... *E05C 3/044* (2013.01); *E05C 7/02* (2013.01); *E05C 19/16* (2013.01); *B01L 2300/043* (2013.01); *B01L 2300/0809* (2013.01); *E05B 65/0042* (2013.01)

(56) References Cited

U.S. PATENT DOCUMENTS

| | | | | |
|---|---|---|---|---|
| 6,120,119 | A * | 9/2000 | Jelinski | B01L 1/02 292/DIG. 21 |
| 6,128,119 | A | 10/2000 | Kamikubo | |
| 6,867,685 | B1 * | 3/2005 | Stillwagon | E05B 5/003 292/341.16 |
| 8,814,284 | B2 * | 8/2014 | Lee | F25D 23/025 312/291 |
| 9,228,386 | B2 * | 1/2016 | Thielmann | E05F 17/002 |
| 2013/0026900 | A1 * | 1/2013 | Oh | F25D 23/02 312/401 |
| 2015/0137674 | A1 * | 5/2015 | Choi | F25D 23/04 312/404 |
| 2018/0318823 | A1 * | 11/2018 | Baumgaertner | E05C 7/02 |

FOREIGN PATENT DOCUMENTS

| | | |
|---|---|---|
| RU | 93460 U1 | 4/2010 |
| SU | 1138 A1 | 3/1926 |
| SU | 650583 A1 | 5/1979 |

OTHER PUBLICATIONS

German Patent and Trademark Office, "Office Action" issued in German patent application No. 10 2017 109 263.3, document of 9 pages, dated Mar. 3, 2018.

German Patent and Trademark Office, "Office Action" issued in German patent application No. 10 2017 109 262.5, document of 6 pages, dated Feb. 9, 2018.

* cited by examiner

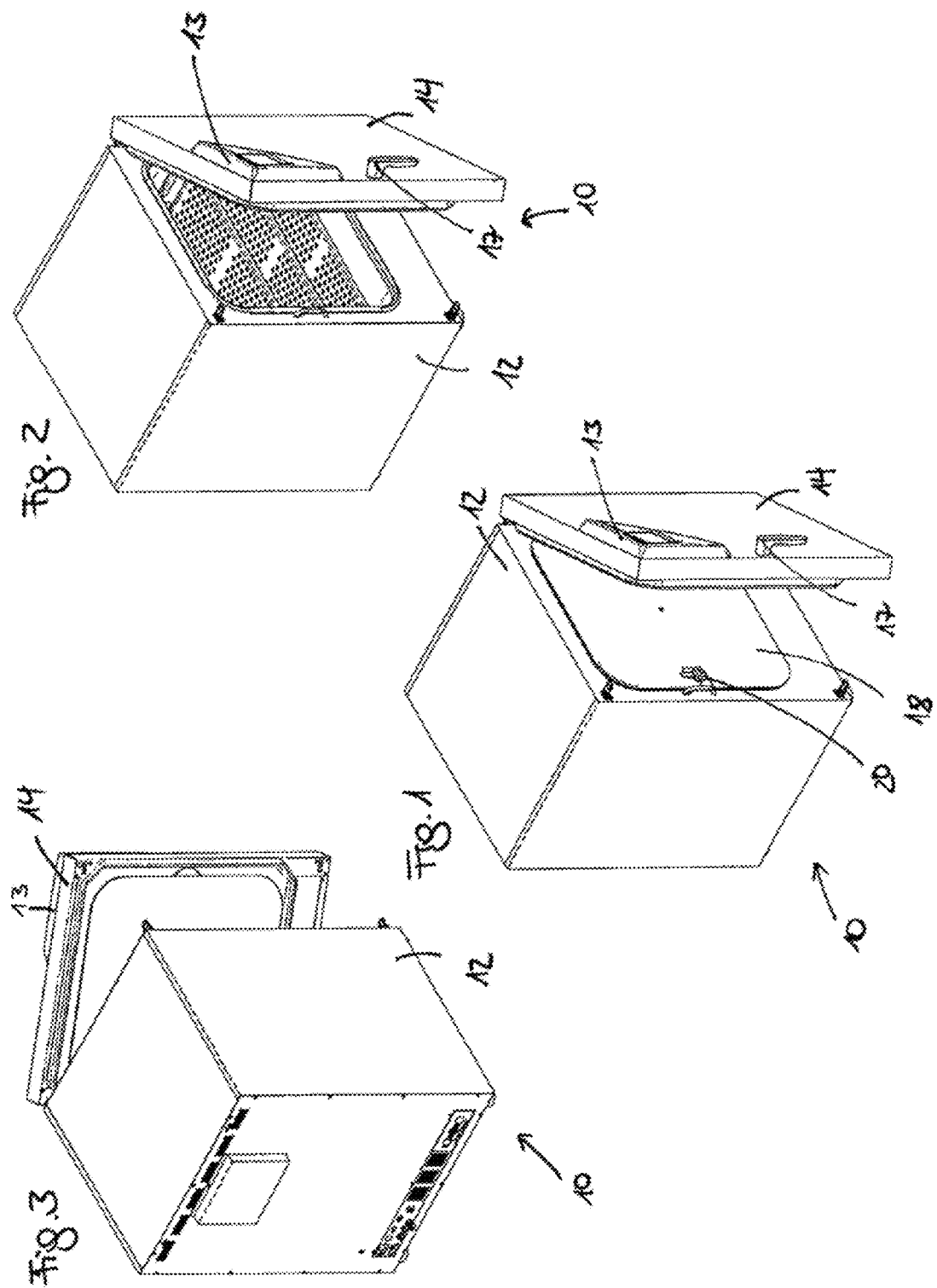

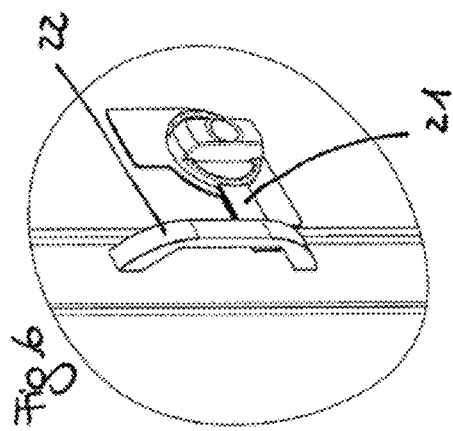
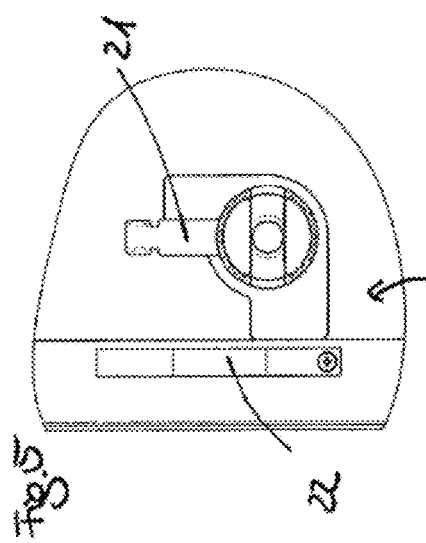
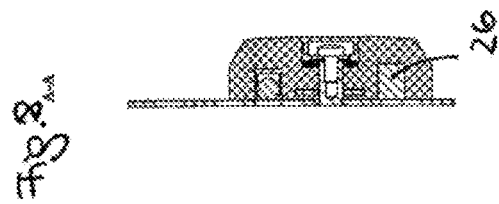
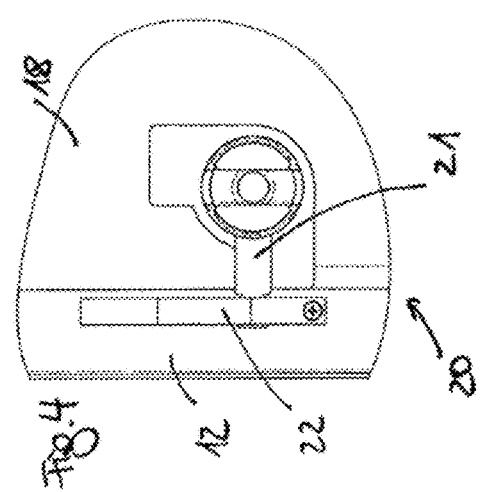
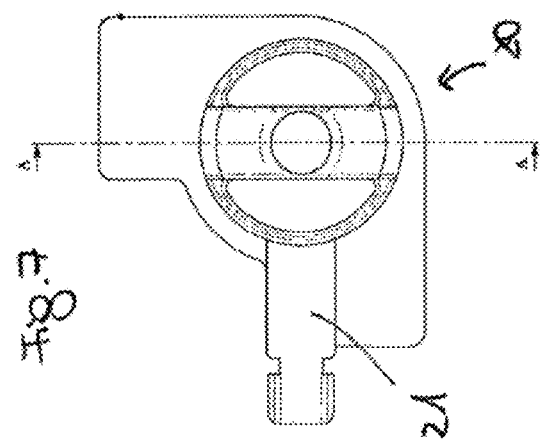

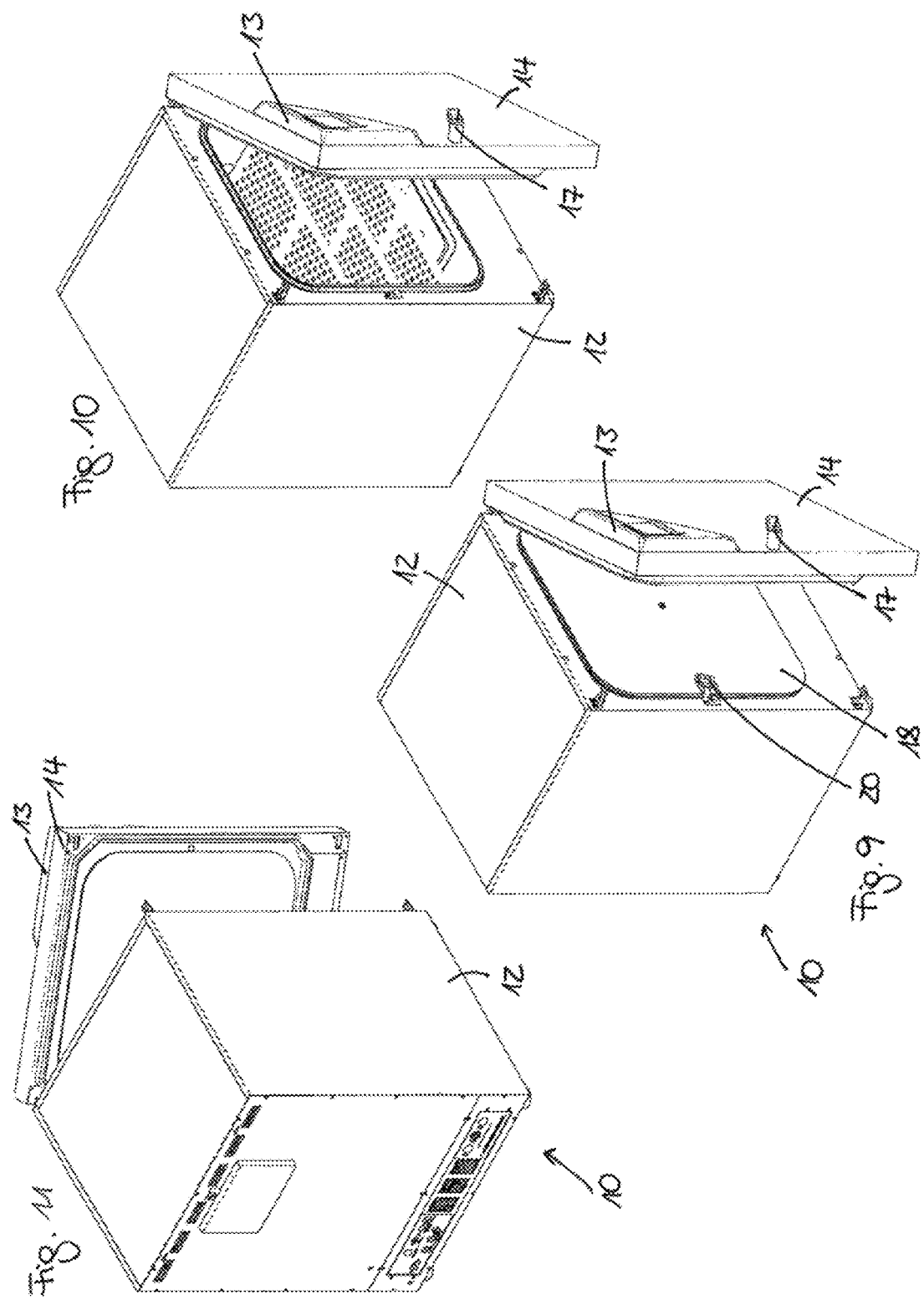

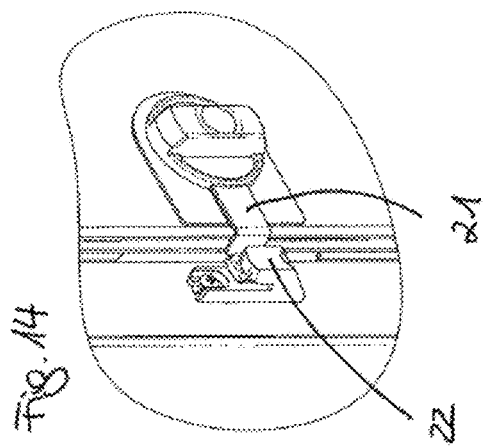
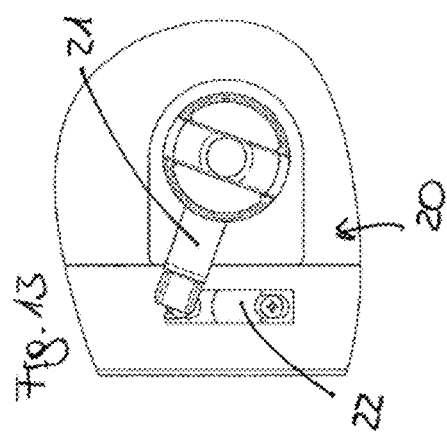
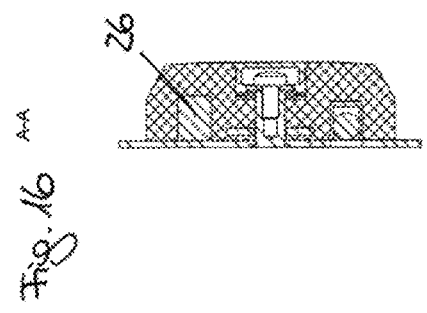
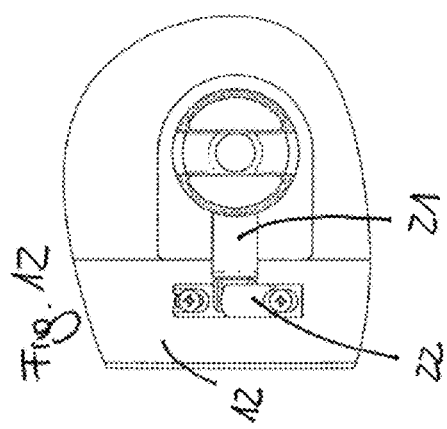
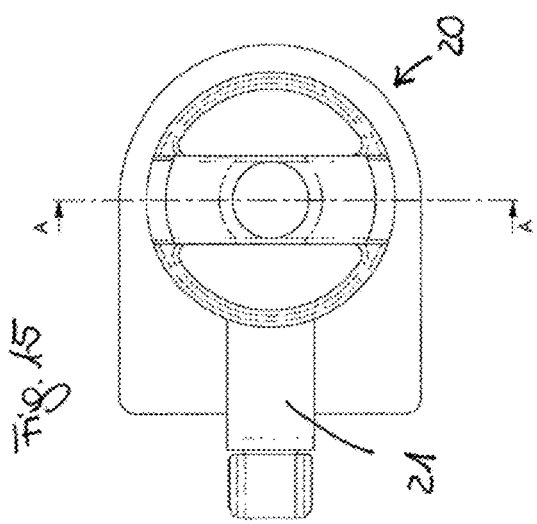

LABORATORY CABINET

CROSS-REFERENCE TO RELATED APPLICATIONS

This application claims priority to German Patent Application No. 10 2017 109 262.5, filed Apr. 28, 2017 and European Patent Application No. 18 000153.9, both of which are incorporated by reference in their entirety.

BACKGROUND

The application relates to a laboratory cabinet having the features and structures disclosed herein.

Previously known are laboratory cabinets with a housing featuring at least one exterior door, which features at least one interior space. Such laboratory cabinets often feature devices by way of which a specific temperature and/or specific climatic conditions, for instance a specific humidity, can be set for the interior space. For instance, cold chambers, heating cabinets, drying cabinets, and incubators are known. In order to prevent that upon the opening of the exterior door, the climatic conditions in the interior space are disturbed, the interior space is known to be closeable by an interior door. The exterior door insulates the interior space of the laboratory cabinet from the surroundings. The interior door prevents an exchange of air between the interior space and the surroundings upon the opening of the exterior door. The interior may be made out of a transparent material, which makes it possible to look into the interior space, without disturbing the climatic conditions in the interior space.

In customary laboratory cabinets, it is necessary for a user to first open the exterior door of the laboratory cabinet before he can open the interior door by way of a second handle.

SUMMARY

The disclosure provides a laboratory cabinet that is more user-friendly to use, and in particular, that opening the interior is simplified.

The application provides a laboratory cabinet having the features and structures disclosed herein.

Advantageous embodiments and further developments are disclosed.

A laboratory cabinet, for instance a cold chamber, a heating cabinet, a drying cabinet, or an incubator can have a housing featuring at least one exterior door, which features at least one interior space that is closeable by way of an interior, is characterized in that the laboratory cabinet has adjustable means, and that as a function of the position of these means, the interior door can be opened together with the exterior door or independently of the exterior door, such that the means are inaccessible when the exterior door is closed. A laboratory cabinet of such design allows the user to specify whether or not upon the opening of the exterior door the interior door should be opened as well, but prevents an unauthorized or unintended change of this setting.

Advantageously, the means are embodied as an adjustable bolt which is easy to operate and is not very prone to failure.

It is preferential in particular that the means are embodied as a swiveling bolt, which may be arranged in a space-saving manner.

The bolt may, for instance, engage a bracket, the bracket being attached either on both sides or only one side, and may therefore may specifically be embodied such that one side is open. The bracket may be embodied as capable of swiveling.

One embodiment provides that the interior door features an interior door locking mechanism, and that the means are formed by this interior door locking mechanism. The interior door locking mechanism is embodied in such a manner that in an open position, it allows for swinging the interior door relative to the housing, and that in a closed position, it secures the interior door against swinging relative to the housing. The interior door locking mechanism is therefore adjustable, and it makes possible for opening the interior door either together with the exterior door or independently of the exterior door as a function of the position of the means. In the event that the interior door locking mechanism is locked prior to the closing of the exterior door, the exterior door can be opened and closed independently of the interior door. In the event that the interior door locking mechanism remains in the open position, the joint opening of the interior door with the exterior door is possible, specifically by way of an additional device, for instance in the form of a catch.

Preferentially, a detachable catch is embodied between the exterior door and the interior door. A catch forms a link here between the exterior door and the interior door, such that upon the opening of the exterior door, the interior door is carried along, specifically pulled along. If the catch is detachable, there may be an option to determine whether the catch should form a link between the exterior door and the interior door, or not.

According to an embodiment, the catch is embodied as a permanent magnet arranged on either the exterior door or on the interior door, which interacts with the other of the exterior door and the interior door, or with a different magnetic element arranged on the other of the exterior door and the interior door. By way of a thus designed catch, a magnetic link is generated between the interior door and the exterior door, which advantageously also allows for a relative movement between the interior door and the exterior door when the two doors are swung around different pivot points, since the magnetic link can be embodied such that the permanent magnet slides over the magnetic element in order to compensate for the relative movement between the two doors.

One embodiment provides that the interior door must be made at least partially out of a transparent material, specifically glass. This makes it possible to look into the interior space without opening the interior door, and therefore without disturbing the climatic conditions in the interior space.

BRIEF DESCRIPTION OF THE DRAWINGS

The disclosure is explained in detail based on the following figures. The figures show as follows:

FIG. 1 shows a perspective view of a first exemplary embodiment of a laboratory cabinet with an opened exterior door;

FIG. 2 shows a perspective view of the laboratory cabinet according to FIG. 1 with an opened exterior door and an opened interior door;

FIG. 3 shows an additional perspective view of the laboratory cabinet according to FIG. 2;

FIG. 4 shows an enlarged representation of the interior door locking mechanism of the laboratory cabinet according to FIG. 1, with the interior door locking mechanism in a closed position;

FIG. 5 shows an enlarged representation of the interior door locking mechanism of the laboratory cabinet according to FIG. 1, with the interior door locking mechanism in an open position;

FIG. 6 shows an additional perspective view of the interior door locking mechanism according to FIG. 4;

FIG. 7 shows a top view on the interior door locking mechanism according to FIG. 4, FIG. 8 shows a longitudinal section along the line A-A through the interior door locking mechanism according to FIG. 7;

FIG. 9 shows a perspective view of a second exemplary embodiment of a laboratory cabinet with an opened exterior door;

FIG. 10 shows a perspective view of the laboratory cabinet according to FIG. 9 with an opened exterior door and an opened interior door;

FIG. 11 shows an additional perspective view of the laboratory cabinet according to FIG. 10;

FIG. 12 shows an enlarged representation of the interior door locking mechanism of the laboratory cabinet according to FIG. 9, with the interior door locking mechanism in a closed position;

FIG. 13 shows an enlarged representation of the interior door locking mechanism of the laboratory cabinet according to FIG. 9, with the interior door locking mechanism in an open position;

FIG. 14 shows an additional perspective view of the interior door locking mechanism according to FIG. 12;

FIG. 15 shows a top view on the interior door locking mechanism according to FIG. 12, FIG. 16 shows a longitudinal section along the line A-A through the interior door locking mechanism according to FIG. 15.

DETAILED DESCRIPTION

FIGS. 1 through 3 show various perspective views of a first exemplary embodiment. FIGS. 9 through 11 show various perspective views of a second exemplary embodiment of a laboratory cabinet 10, which may be embodied, for instance, as a cold chamber, a heating cabinet, a drying cabinet, or an incubator. The following elaborations apply to both exemplary embodiments, unless it is explicitly otherwise specified.

The laboratory cabinet 10 features a housing 12 with an exterior door 14, which encloses an interior space. The housing 12 may feature a base side, a top side, two side walls positioned opposite of each other, and a rear wall, such that an aperture positioned opposite of the rear wall can be closed by way of the exterior door 14. The exterior door 14 may be closed by way of an exterior door locking mechanism, which may be actuated by way of a handle 17. The exterior door locking mechanism secures the exterior door 14 against unintended swinging. A further blocking mechanism may be provided to prevent the unlocking of the exterior door locking mechanism.

The housing 12 may be embodied with a double wall for better heat insulation. Specifically, it may feature an inner chamber. The laboratory cabinet 10 features at least one interior door 18, which seals an aperture of the interior space facing the exterior door 14 in order to prevent or reduce an exchange of air between the interior space of the inner chamber and the surroundings when the exterior door 14 is opened.

The interior door 18 features an interior door locking mechanism 20, which secures the interior door 18 when in a closed position against swinging. The interior door 18 may further feature a blocking mechanism, which prevents the interior door locking mechanism 20 from being opened.

The interior door 18 may be made at least partially or fully out of a transparent material, such as glass.

The interior space may be subdivided into multiple partial spaces, each of which being closed by way of a respective separate interior door 18, such that only one of the interior doors 18 has to be opened when sample material must be placed in the laboratory cabinet 10, specifically in one of the partial spaces, or removed from it, with as little as possible disturbance caused to the climatic conditions in the other partial spaces.

On the outer side of the enclosure 12, a control panel 13 may be arranged, by way of which specifically the climatic conditions in the interior space of the laboratory cabinet 10, for instance the temperature or the humidity, can be set.

The laboratory cabinet 10 may feature two or multiple exterior doors 14.

FIGS. 4 through 8 show various detail views of the interior door locking mechanism 20 of the laboratory cabinet 10 shown in FIGS. 1 through 3; FIGS. 12 through 16 show various detail views of the interior door locking mechanism 20 of laboratory cabinet 10 shown in FIGS. 9 through 11.

The laboratory cabinet 10 features adjustable means 20, such that as a function of the position of the means 20, the interior door 18 can be opened together with the exterior door 14 or independently of the exterior door 14, such that the means 20 are inaccessible when the exterior door 14 is closed.

The means 20 may feature a bolt 21 that can be moved between an open position (cf. FIG. 5 and FIG. 13) and a closed position (cf. FIG. 4 and FIG. 12). For these purposes, the bolt engages a bracket 22 when in the closed position, whereas in the open position it is disengaged from the bracket 22. The bracket 22 may be attached on both sides (cf. FIGS. 4 through 6) or be attached on one side and open on the other side (cf. FIGS. 12 through 14) or be embodied so as to be able to swivel. In particular, the bolt 21 is arranged on the interior door 18, whereas the bracket 22 is arranged on the housing 12, specifically on a front face of one of the side walls of the enclosure 12 facing the exterior door 14. By way of this arrangement, the bolt 21 and the bracket 22 are covered by the exterior door 14 when the exterior door 14 is closed, such that the means 20 are inaccessible when the exterior door 14 is closed. In particular, the bolt 21 is embodied as a rotating bolt.

There is a possibility of securing the bolt 21 in the open position by way of a latching mechanism in order to obstruct an unintended shifting of the bolt 21.

Preferentially, the means 20 simultaneously constitute an interior door locking mechanism, which secures the interior door 18 against swinging relative to the housing 12 when it is in a closed position, whereas in an open position a swinging of the interior door 18 against the housing 12 is allowed.

A detachable catch may be arranged between the exterior door 14 and the interior door 18. In particular, the catch is embodied as at least one permanent magnet 26. The permanent magnet 26 may be arranged on the interior door 18 or on the exterior door 14. In the present exemplary embodiment, it is arranged on the interior door 18, specifically on the bolt 21. Since when the exterior door 14 is closed, the interior door locking mechanism 20 is almost in contact with the exterior door 14, or advantageously, it may come to be positioned in a recess on the interior side of the exterior door 14, and since furthermore, the interior side of the exterior door 14 is made out of a magnetizing material, or alternatively, a magnetizing element is arranged on the interior side of the exterior door 14, the interior door 18 is attracted magnetically by the exterior door 14 and carried along when the exterior door 14 is opened. In particular, the magnetic link between interior door 18 and the exterior door 14 may compensate the relative movement between the interior door 18 and the exterior door 14 in that the permanent magnet 41 slides over the inner surface of the exterior door 14.

The following options exist, among others, for the operation of the doors 14, 18: If prior to the closing of the exterior door 14, the interior door 18 was closed by way of the means 20 in such a manner that the bolt 21 was put into the closed position, the exterior door 14 may be opened independently of the interior door 18, since upon the opening of the exterior door 14, the magnetic link between the interior door 18 and the exterior door 14 is severed, since the interior door 18 is kept by the bolt 21 in the closed position. If, however, prior to the closing of the exterior door 14, the bolt 21 was put into the open position, upon the closing of the exterior door 14, the interior door 18 is closed as well, and upon the opening of the exterior door 14, the interior door 18 is carried along due to the magnetic link between the interior door 18 and the exterior door 14, such that the interior door 18 is opened together with the exterior door 14.

REFERENCE LIST 10 laboratory cabinet
13 control panel
12 housing
14 exterior door
16 exterior door locking mechanism
17 handle
18 interior door
20 means
21 bolt
22 bracket
26 permanent magnet

The invention claimed is:

1. A laboratory cabinet, comprising:
a housing with an interior space;
an interior door that closes the interior space;
an exterior door;
an adjustable device;
wherein when the adjustable device is in a first position, the interior door opens together with the exterior door;
wherein when the adjustable device is in a second position, the exterior door is openable while the interior door remains closed, and the interior door opens independently of the exterior door; and
wherein the adjustable device is inaccessible when the exterior door is closed.

2. The laboratory cabinet according to claim 1, wherein the adjustable device is an adjustable bolt.

3. The laboratory cabinet according to claim 1, wherein the adjustable device is a swiveling bolt.

4. The laboratory cabinet according to claim 1, wherein the interior door has an interior door lock, and the adjustable device is formed by the interior door lock.

5. The laboratory cabinet according to claim 1, further comprising a detachable catch between the exterior door and the interior door.

6. The laboratory cabinet according to claim 5, wherein the catch is a permanent magnet arranged on either the exterior door or the interior door, wherein the permanent magnet interacts with the exterior door, the interior door, or with a different magnetizing element arranged on the exterior door or the interior door.

7. The laboratory cabinet according to claim 1, wherein the interior door is made at least partially out of a transparent material.

8. A laboratory cabinet, comprising:
a housing with an interior space and an aperture opening to an external ambient environment;
an interior door that seals the aperture opening;
an exterior door that closes over the interior door, wherein the interior door is between the exterior door and the interior space;
an adjustable device;
wherein when the adjustable device is in a first state, the interior door opens together with the exterior door;
wherein when the adjustable device is in a second state, the exterior door is openable while the interior door remains closed, and the interior door opens independently of the exterior door; and
wherein the adjustable device is inaccessible when the exterior door is closed.

9. The laboratory cabinet according to claim 8, wherein the adjustable device is an adjustable bolt.

10. The laboratory cabinet according to claim 8, wherein the adjustable device is a swiveling bolt.

11. The laboratory cabinet according to claim 8, wherein the interior door has an interior door lock, and the adjustable device is formed by the interior door lock.

12. The laboratory cabinet according to claim 8, further comprising a detachable catch between the exterior door and the interior door.

13. The laboratory cabinet according to claim 12, wherein the catch is a magnet arranged on the exterior door, wherein the magnet interacts with the interior door.

14. The laboratory cabinet according to claim 12, wherein the catch is a magnet arranged on the interior door, and wherein the magnet interacts with the exterior door.

15. A laboratory cabinet, comprising:
a housing with an interior space and an aperture opening to an external ambient environment;
an interior door that closes the aperture opening;
an exterior door that closes over the interior door, wherein the interior door is between the exterior door and the interior space;
an adjustable device, the adjustable device being adjustable between a door cooperating condition and a door independent condition;
wherein, when the adjustable device is in the door cooperating condition, the interior door opens together with the exterior door;
wherein, when the adjustable device is in the door independent condition, the interior door opens and closes independent of opening and closing exterior door;
wherein the adjustable device is inaccessible when the exterior door is closed.

16. The laboratory cabinet according to claim 15, wherein the adjustable device is selected from the group consisting of an adjustable bolt and a swiveling bolt.

17. The laboratory cabinet according to claim 15, wherein the adjustable device locks the interior door.

18. The laboratory cabinet according to claim 15, further comprising a detachable catch between the exterior door and the interior door.

19. The laboratory cabinet according to claim 18, wherein the catch is a magnet arranged on the exterior door, and wherein the magnet interacts with the interior door.

20. The laboratory cabinet according to claim 18, wherein the catch is a magnet arranged on the interior door, wherein the magnet interacts with the exterior door.

* * * * *